US008236342B2

(12) United States Patent
Thomas et al.

(10) Patent No.: US 8,236,342 B2
(45) Date of Patent: Aug. 7, 2012

(54) MULTI-POLYMER HYDROGELS

(75) Inventors: Brian Thomas, Columbia City, IN (US); Kai Zhang, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 106 days.

(21) Appl. No.: 12/767,016

(22) Filed: Apr. 26, 2010

(65) Prior Publication Data
US 2010/0204800 A1 Aug. 12, 2010

Related U.S. Application Data

(62) Division of application No. 11/833,549, filed on Aug. 3, 2007, now Pat. No. 7,731,988.

(51) Int. Cl.
A61F 2/32 (2006.01)
A61F 2/38 (2006.01)
A61F 2/40 (2006.01)
A61F 2/44 (2006.01)
A61F 2/42 (2006.01)

(52) U.S. Cl. .............. 424/423; 623/19.11; 623/23.58; 623/22.11; 623/20.14; 623/20.11; 525/50; 525/56; 525/55; 525/452; 525/474; 525/57

(58) Field of Classification Search ............... None
See application file for complete search history.

(56) References Cited

U.S. PATENT DOCUMENTS

| | | |
|---|---|---|
| 3,200,178 A | 8/1965 | Kanji |
| 3,862,265 A | 1/1975 | Steinkamp et al. |
| 3,875,302 A | 4/1975 | Inoue |
| 4,036,788 A | 7/1977 | Steckler |
| 4,058,491 A | 11/1977 | Steckler |
| 4,060,678 A | 11/1977 | Steckler |
| 4,071,508 A | 1/1978 | Steckler |
| 4,279,795 A | 7/1981 | Yamashita et al. |
| 4,300,820 A | 11/1981 | Shah |
| 4,379,874 A | 4/1983 | Stoy |
| 4,451,599 A | 5/1984 | Odorzynski et al. |
| 4,451,630 A | 5/1984 | Atkinson et al. |
| 4,464,438 A | 8/1984 | Lu |
| 4,472,542 A | 9/1984 | Nambu |
| 4,640,941 A | 2/1987 | Park et al. |
| 4,656,216 A | 4/1987 | Muller et al. |
| 4,663,358 A | 5/1987 | Hyon et al. |
| 4,664,857 A | 5/1987 | Nambu |
| 4,699,146 A | 10/1987 | Sieverding |
| 4,734,097 A | 3/1988 | Tanabe et al. |
| 4,771,089 A | 9/1988 | Ofstead |
| 4,772,287 A | 9/1988 | Ray et al. |
| 4,808,353 A | 2/1989 | Nambu et al. |
| 4,842,597 A | 6/1989 | Brook |
| 4,851,168 A | 7/1989 | Graiver et al. |
| 4,859,719 A | 8/1989 | Ofstead |
| 4,871,490 A | 10/1989 | Rosiak et al. |
| 4,874,562 A | 10/1989 | Hyon et al. |
| 4,915,974 A | 4/1990 | D'Amelia et al. |
| 4,956,122 A | 9/1990 | Watts et al. |
| 4,966,924 A | 10/1990 | Hyon et al. |
| 4,988,761 A | 1/1991 | Ikada et al. |
| 5,028,648 A | 7/1991 | Famili et al. |
| 5,047,055 A | 9/1991 | Bao et al. |
| 5,053,455 A | 10/1991 | Kroggel et al. |
| 5,106,876 A | 4/1992 | Kawamura |
| 5,118,779 A | 6/1992 | Szycher |
| 5,122,565 A | 6/1992 | George |
| 5,157,093 A | 10/1992 | Harisiades et al. |
| 5,189,097 A | 2/1993 | LaFleur et al. |
| 5,192,326 A | 3/1993 | Bao et al. |
| 5,244,799 A | 9/1993 | Anderson |
| 5,276,079 A | 1/1994 | Duan et al. |
| 5,288,503 A | 2/1994 | Wood et al. |
| 5,306,311 A | 4/1994 | Stone et al. |
| 5,311,223 A | 5/1994 | Vanderlaan |

(Continued)

FOREIGN PATENT DOCUMENTS

| | | |
|---|---|---|
| EP | 0256293 | 2/1988 |
| EP | 0290616 | 11/1988 |
| EP | 0365108 | 4/1990 |
| EP | 0505634 | 9/1992 |
| EP | 0696210 | 2/1996 |
| EP | 0738762 | 4/1996 |
| EP | 0784987 | 7/1997 |
| EP | 0835143 | 4/1998 |
| EP | 0845480 | 6/1998 |
| EP | 0927053 | 7/1999 |

(Continued)

OTHER PUBLICATIONS

Molecular Principles of Biomaterials,"Lecture 7 Hydrogel Biomaterials: Structure and Physical Chemistry", Spring 2003, 8 pages.

(Continued)

*Primary Examiner* — Robert A Wax
*Assistant Examiner* — Danah Al-Awadi
(74) *Attorney, Agent, or Firm* — Schwegman, Lundberg & Woessner, P.A.

(57) ABSTRACT

The invention provides a multi-polymer hydrogel article having a first polymeric, water-swellable material and a second polymeric material, organized such that a first region substantially comprises the first polymeric, water-swellable material, a second region adjacent the first region comprises a mixture of the first polymeric, water-swellable material and the second polymeric material, and a third region adjacent the second region substantially comprises the second polymeric material. The article exhibits an increasing concentration gradient of the second polymeric material moving from the first region, through the second region, to the third region. The invention also provides methods for forming a multi-polymer hydrogel article by (a) forming a hydrogel structure using a first polymeric, water-swellable material, (b) creating an aerogel structure having a plurality of open pores by dehydrating the hydrogel structure, (c) contacting the aerogel structure with a second polymeric material to incorporate the second polymeric material into at least a portion of the plurality of open pores to form the multi-polymer hydrogel article, and (d) rehydrating the multi-polymer hydrogel article.

13 Claims, No Drawings

U.S. PATENT DOCUMENTS

| | | | |
|---|---|---|---|
| 5,315,478 A | 5/1994 | Cadwell et al. | |
| 5,334,634 A | 8/1994 | Bastiolo et al. | |
| 5,336,551 A | 8/1994 | Graiver et al. | |
| 5,358,525 A | 10/1994 | Fox et al. | |
| 5,360,830 A | 11/1994 | Bastioli et al. | |
| 5,362,803 A | 11/1994 | LaFleur et al. | |
| 5,407,055 A | 4/1995 | Tanaka | |
| 5,409,966 A | 4/1995 | Duan et al. | |
| 5,410,016 A | 4/1995 | Hubbell et al. | |
| 5,458,643 A | 10/1995 | Oka et al. | |
| 5,527,271 A | 6/1996 | Shah et al. | |
| 5,540,033 A | 7/1996 | Fox et al. | |
| 5,552,096 A | 9/1996 | Auda et al. | |
| 5,576,072 A | 11/1996 | Hostettler et al. | |
| 5,580,938 A | 12/1996 | Gutweiler et al. | |
| 5,624,463 A | 4/1997 | Stone et al. | |
| 5,632,774 A | 5/1997 | Babian | |
| 5,674,295 A | 10/1997 | Ray et al. | |
| 5,681,300 A | 10/1997 | Ahr et al. | |
| 5,705,296 A | 1/1998 | Kamauchi et al. | |
| 5,709,854 A | 1/1998 | Griffith-Cima et al. | |
| 5,711,960 A | 1/1998 | Shikinami | |
| 5,716,404 A | 2/1998 | Vacanti et al. | |
| 5,723,331 A | 3/1998 | Tubo et al. | |
| 5,834,029 A | 11/1998 | Bellamkonda et al. | |
| 5,879,713 A | 3/1999 | Roth et al. | |
| 5,891,826 A | 4/1999 | Tsaur et al. | |
| 5,941,909 A | 8/1999 | Purkait | |
| 5,976,186 A | 11/1999 | Bao et al. | |
| 5,981,826 A | 11/1999 | Ku et al. | |
| 6,015,576 A | 1/2000 | See et al. | |
| 6,017,577 A | 1/2000 | Hostettler et al. | |
| 6,040,493 A | 3/2000 | Cooke et al. | |
| 6,080,488 A | 6/2000 | Hostettler et al. | |
| 6,117,449 A | 9/2000 | See et al. | |
| 6,120,904 A | 9/2000 | Hostettler et al. | |
| 6,121,341 A | 9/2000 | Sawhney et al. | |
| 6,129,761 A | 10/2000 | Hubbell | |
| 6,129,791 A | 10/2000 | Nakajima et al. | |
| 6,132,468 A | 10/2000 | Mansmann | |
| 6,139,963 A | 10/2000 | Fujii et al. | |
| 6,146,686 A | 11/2000 | Leitao | |
| 6,156,345 A | 12/2000 | Chudzik et al. | |
| 6,156,572 A | 12/2000 | Bellamkonda et al. | |
| 6,162,456 A | 12/2000 | Dunbar et al. | |
| 6,180,132 B1 | 1/2001 | Huang et al. | |
| 6,180,606 B1 | 1/2001 | Chen et al. | |
| 6,184,197 B1 | 2/2001 | Heinzman et al. | |
| 6,187,048 B1 | 2/2001 | Milner | |
| 6,207,185 B1 | 3/2001 | See et al. | |
| 6,211,296 B1 | 4/2001 | Frate et al. | |
| 6,224,893 B1 | 5/2001 | Langer et al. | |
| 6,231,605 B1 | 5/2001 | Ku | |
| 6,232,406 B1 | 5/2001 | Stoy | |
| 6,238,691 B1 | 5/2001 | Huang | |
| 6,268,405 B1 | 7/2001 | Yao et al. | |
| 6,271,278 B1 | 8/2001 | Park et al. | |
| 6,280,475 B1 | 8/2001 | Bao et al. | |
| 6,306,424 B1 | 10/2001 | Vyakarnam et al. | |
| 6,365,149 B2 | 4/2002 | Vyakarnam et al. | |
| 6,371,984 B1 | 4/2002 | Van Dyke et al. | |
| 6,372,283 B1 | 4/2002 | Shim et al. | |
| 6,375,634 B1 | 4/2002 | Carroll | |
| 6,387,325 B1 | 5/2002 | Keusch et al. | |
| 6,402,784 B1 | 6/2002 | Wardlaw | |
| 6,443,988 B2 | 9/2002 | Felt et al. | |
| 6,509,098 B1 | 1/2003 | Merrill et al. | |
| 6,531,147 B2 | 3/2003 | Sawhney et al. | |
| 6,533,817 B1 | 3/2003 | Norton et al. | |
| 6,583,219 B2 | 6/2003 | Won et al. | |
| 6,602,952 B1 | 8/2003 | Bentley et al. | |
| 6,608,117 B1 | 8/2003 | Gvozdic | |
| 6,620,196 B1 | 9/2003 | Trieu | |
| 6,626,945 B2 | 9/2003 | Simon et al. | |
| 6,629,997 B2 | 10/2003 | Mansmann | |
| 6,630,457 B1 | 10/2003 | Aeschilmann et al. | |
| 6,632,246 B2 | 10/2003 | Simon et al. | |
| 6,645,517 B2 | 11/2003 | West et al. | |
| 6,692,738 B2 | 2/2004 | MacLaughlin et al. | |
| 6,706,690 B2 | 3/2004 | Reich et al. | |
| 6,709,668 B2 | 3/2004 | Won et al. | |
| 6,710,104 B2 | 3/2004 | Haraguchi | |
| 6,710,126 B1 | 3/2004 | Hirt et al. | |
| 6,723,781 B1 | 4/2004 | Frate et al. | |
| 6,730,298 B2 | 5/2004 | Griffith-Cima et al. | |
| 6,733,533 B1 | 5/2004 | Lozier | |
| 6,780,840 B1 | 8/2004 | DeVore et al. | |
| 6,783,546 B2 | 8/2004 | Zucherman et al. | |
| 6,783,721 B2 | 8/2004 | Higham et al. | |
| 6,803,420 B2 | 10/2004 | Cleary et al. | |
| 6,852,772 B2 | 2/2005 | Muratoglu et al. | |
| 6,855,743 B1 | 2/2005 | Gvozdic | |
| 6,861,067 B2 | 3/2005 | McGhee et al. | |
| 7,235,592 B2 | 6/2007 | Muratoglu et al. | |
| 7,531,000 B2 | 5/2009 | Hodorek | |
| 2001/0026810 A1 | 10/2001 | McGhee et al. | |
| 2001/0032019 A1 | 10/2001 | Van Dyke et al. | |
| 2001/0049417 A1 | 12/2001 | Frate et al. | |
| 2001/0053897 A1 | 12/2001 | Frate et al. | |
| 2002/0022884 A1 | 2/2002 | Mansmann | |
| 2002/0026244 A1 | 2/2002 | Trieu | |
| 2002/0029083 A1 | 3/2002 | Zucherman et al. | |
| 2002/0049498 A1 | 4/2002 | Yuksel et al. | |
| 2002/0131952 A1 | 9/2002 | Hennink et al. | |
| 2002/0151979 A1 | 10/2002 | Lambrecht et al. | |
| 2002/0173855 A1 | 11/2002 | Mansmann | |
| 2002/0193531 A1 | 12/2002 | Stoy et al. | |
| 2003/0008396 A1 | 1/2003 | Ku | |
| 2003/0065389 A1 | 4/2003 | Petersen | |
| 2003/0080465 A1 | 5/2003 | Higham et al. | |
| 2003/0099709 A1 | 5/2003 | Shah et al. | |
| 2003/0130427 A1 | 7/2003 | Cleary et al. | |
| 2003/0152528 A1 | 8/2003 | Singh et al. | |
| 2003/0170308 A1 | 9/2003 | Cleary et al. | |
| 2003/0195628 A1 | 10/2003 | Bao et al. | |
| 2003/0232895 A1 | 12/2003 | Omidian et al. | |
| 2003/0236323 A1 | 12/2003 | Ratner et al. | |
| 2004/0002764 A1 | 1/2004 | Gainor et al. | |
| 2004/0005423 A1 | 1/2004 | Dalton et al. | |
| 2004/0030392 A1 | 2/2004 | Lambrecht et al. | |
| 2004/0039447 A1 | 2/2004 | Simon et al. | |
| 2004/0092653 A1 | 5/2004 | Ruberti et al. | |
| 2004/0096509 A1 | 5/2004 | Hutchens et al. | |
| 2004/0116641 A1 | 6/2004 | Mather et al. | |
| 2004/0121951 A1 | 6/2004 | Rhee | |
| 2004/0127618 A1 | 7/2004 | Ulmer | |
| 2004/0127992 A1 | 7/2004 | Serhan | |
| 2004/0131582 A1 | 7/2004 | Grinstaff et al. | |
| 2004/0133280 A1 | 7/2004 | Trieu | |
| 2004/0143329 A1 | 7/2004 | Ku | |
| 2004/0147673 A1 | 7/2004 | Calabro | |
| 2004/0153163 A1 | 8/2004 | Posner | |
| 2004/0161444 A1 | 8/2004 | Song et al. | |
| 2004/0171740 A1 | 9/2004 | Ruberti et al. | |
| 2004/0199250 A1 | 10/2004 | Fell | |
| 2004/0220296 A1 | 11/2004 | Lowman et al. | |
| 2004/0242770 A1 | 12/2004 | Feldstein et al. | |
| 2004/0244978 A1 | 12/2004 | Shaarpour | |
| 2005/0004560 A1 | 1/2005 | Cox | |
| 2005/0027069 A1 | 2/2005 | Rhee et al. | |
| 2005/0048103 A1 | 3/2005 | Cleary et al. | |
| 2005/0049365 A1 | 3/2005 | Cleary et al. | |
| 2005/0075454 A1 | 4/2005 | Plochocka et al. | |
| 2005/0095296 A1 | 5/2005 | Lowman et al. | |
| 2005/0107561 A1 | 5/2005 | Lee et al. | |
| 2005/0197441 A1 | 9/2005 | Shibutani et al. | |
| 2006/0078587 A1 | 4/2006 | Leong | |
| 2006/0141002 A1 | 6/2006 | Liu et al. | |
| 2006/0188487 A1 | 8/2006 | Thomas et al. | |
| 2007/0004861 A1 | 1/2007 | Cai | |
| 2007/0134333 A1* | 6/2007 | Thomas et al. ............. 424/486 |
| 2007/0202323 A1 | 8/2007 | Kleiner et al. | |
| 2007/0293651 A1 | 12/2007 | Tada | |
| 2008/0090145 A1 | 4/2008 | Hiwara | |
| 2009/0053318 A1 | 2/2009 | Tan et al. | |

FOREIGN PATENT DOCUMENTS

| | | |
|---|---|---|
| EP | 1079224 | 2/2001 |
| EP | 1174463 | 1/2002 |
| EP | 1593400 | 11/2005 |
| EP | 1595899 | 11/2005 |
| FR | 2786400 | 6/2000 |
| FR | 2865939 | 8/2005 |
| FR | 2866571 | 8/2005 |
| GB | 2338958 | 10/2000 |
| JP | 01178545 | 7/1989 |
| JP | 01305959 | 12/1989 |
| JP | 03141957 | 6/1991 |
| JP | 04303444 | 10/1992 |
| JP | 09124730 | 5/1997 |
| JP | 09124731 | 5/1997 |
| JP | 10036534 | 2/1998 |
| JP | 10043286 | 2/1998 |
| JP | 10306534 | 2/1998 |
| WO | WO 90/15082 | 12/1990 |
| WO | WO/94/13235 | 6/1994 |
| WO | WO 94/17851 | 8/1994 |
| WO | WO/95/02616 | 1/1995 |
| WO | WO/95/26699 | 10/1995 |
| WO | WO 96/40304 | 12/1996 |
| WO | WO 98/17215 | 4/1998 |
| WO | WO 98/53768 | 12/1998 |
| WO | WO 99/03454 | 1/1999 |
| WO | WO 99/13923 | 3/1999 |
| WO | WO/99/67320 | 12/1999 |
| WO | WO 01/17574 | 3/2001 |
| WO | WO/01/19283 | 3/2001 |
| WO | WO 01/77197 | 10/2001 |
| WO | WO/02/04570 | 1/2002 |
| WO | WO 02/13871 | 2/2002 |
| WO | WO 02/060501 | 8/2002 |
| WO | WO 02/087642 | 11/2002 |
| WO | WO 02/087645 | 11/2002 |
| WO | WO 03/008007 | 1/2003 |
| WO | WO 03/074099 | 9/2003 |
| WO | WO/03/082359 | 10/2003 |
| WO | WO 2004/007651 | 1/2004 |
| WO | WO 2004/029174 | 4/2004 |
| WO | WO 2004/031253 | 4/2004 |
| WO | WO 2004/047690 | 6/2004 |
| WO | WO 2004/055057 | 7/2004 |
| WO | WO 2004/060427 | 7/2004 |
| WO | WO 2004/063388 | 7/2004 |
| WO | WO/2004/064693 | 8/2004 |
| WO | WO 2004/066704 | 8/2004 |
| WO | WO 2004/069296 | 8/2004 |
| WO | WO 2004/072138 | 8/2004 |
| WO | WO 2004/093786 | 11/2004 |
| WO | WO/2005/004943 | 1/2005 |
| WO | WO/2005/030382 | 4/2005 |
| WO | WO 2005/035726 | 4/2005 |
| WO | WO 2006/021054 | 3/2006 |
| WO | WO 2006/091706 | 8/2006 |
| WO | WO/2007/067697 | 6/2007 |
| WO | WO 2007/015208 | 8/2007 |
| WO | WO/2008/144514 | 11/2008 |
| WO | WO/2009/020793 | 2/2009 |
| WO | WO/2009/032430 | 3/2009 |
| WO | WO/2009/088654 | 5/2010 |

OTHER PUBLICATIONS

Anseth, Kristi, et al., "In situ Forming degradable networks and their applications in tissue engineering and drug delivery", Journal of Controlled Release, vol. 78, pp. 199-209, 2002.

Babb. David, et al, "Perfluorcyclobutane Aromatic Ether Polymers. III. Synthesis and Thermal Stability of a Thermoset Polymer containing Triphenylphosphine Oxide", Journal of Applied Polymer Science, vol. 69, pp. 2005-2012, 1998.

Bass, Lawrence, et al., "Laser Tissue Welding: A comprehensive Review of Current and Future Clinic Applications", Lasers in Surgery and Medicine, vol. 17, pp. 315-349, 1995.

Bray, James, et al, "Poly(vinyl Alcohol) Hydrogels. Formation by Electron Beam Irradiation of Aqueous Solutions and Subsequent Crystallization," Journal of Applied Polymer Science, vol. 17, pp. 3779-3794, 1973.

Bray, James, et al. "Poly(vinyl alcohol) Hydrogels for synthetic Articular Cartilage Material," Biomed Material Review, vol. 7, pp. 431-443, 1973.

Bryant, Stephanie, et al, "Crosslinking Density Influences Chondrocyte Metabolism in Dynamically Loaded Photocrosslinked Poly(ethylene glycol) Hydrogels", Annals of Biomedical Engineering, vol. 32 No. 3, pp. 407-417, Mar. 2004.

Bryant, Stephanie, et al, "The Effects of Scaffold thickness on tissue engineered cartilage in photocrosslinked poly(ethylene oxide) hydrogels", Biomaterials, vol. 22, pp. 619-628, 2001.

Bryant, Stephanie et al, "Phtocrosslinkable Poly(ethylene oxide) and Poly (vinyl Alcohol) Hydrogels for Tissue Engineering Cartilage", First Joint BMES/EMBS Conference, p. 751, Oct. 1999 Atlanta Georgia.

Carey, F., et al., "Advanced Organic Chemistry, Part B: Reactions and Synthesis", Plenum Publishers, NY, pp. 829, (2001).

Chow, LC, et al., "Octacalcium Phosphate" Monograph in Oral Science, Krager, 2001, vol. 18, "Solubility of Calcium Phosphates" pp. 94-112 and "Amorphous Calcium Phosphate" pp. 130-148.

Covert, Rebeccah, et al., "Friction & Wear Testing of new Biomaterial for use as an Articular Cartilage Substitute", Bioengineering Conference, ASME 2001 pp. 355-356.

Ding, Mei Yee , "Characterisation of Poly vinly-alcohol Hydrogels" May 17, 2003.

Durmaz,S. et al, "Phase Separation during the formation of poly(acrylamide) hydrogels", Polymer, vol. 41, pp. 5729-5735, 2000.

Jenkins, et al., "Glossary of Basic Terms in Polymer Science" IUPAC Recommendations 1996, Pure & Applied Chemical, vol. 68, No. 12, pp. 2287-2311, 1996.

Gong, J. et al., "Friction of Polymer Gels and the Potential Application as Artificial Cartilage", SPIE Conference, vol. 3669, pp. 218-225, Mar. 1999.

Green, Mark, et al., Organic Chemistry Principles and Industrial Practice, Wiley VCH, 2003.

Guilherme, M. et al., "Hydrogels based on PAAm network with PNIPAAm included: hydrophilic-hydrophobic transition measured by the partition of Orange II and Methylene Blue in water", Polymer, vol. 44, pp. 4213-4219, 2003.

Haralabakopoulus, A. et al., "Modification of Poly(vinyl alcohol) Polymers by Aliphatic Carboxylic Acids via Reactive Blending," Journal of Applied Polymer Science, vol. 69, pp. 1885-1890, 1998.

Hassan, Christie, et al, "Diffusional characteristics of freeze/thawed poly(vinyl alcohol) hydrogels: Applications to protein controlled release from multilaminate devices," European Journal of Pharmaceutics and Biopharmeceutics, vol. 49, pp. 161-165. 2000.

Hassan, Christie, et al, "Cellular PVA Hydrogels Produced by Freeze/Thawing," Journal of Applied Polymer Science, vol. 76, pp. 2075-2079, 2000.

Hassan, Christie, et al., "Modeling of crystal dissolution of poly(vinyl alcohol) gels produced by freezing/thawing processes" Polymer, vol. 41, pp. 6729-6739, 2000.

Hassan, Christie, et al, "Structure and Applications of Poly(vinyl alcohol) Hydrogels Produced by Conventional Crosslinking or by Freezing/Thawing Methods", Advances in Polymer Science, vol. 153, pp. 37-65, 2000.

Hassan, Christie, et al, "Structure and Morphology of Freeze/Thawed PVA Hydrogels", Macromolecules, vol. 33, pp. 2472-2479, 2000.

Hickey, Alla, et al, "Solute diffusion in poly(vinyl alcohol)/poly(acrylic acid) composition membranes prepared by freezing/thawing techniques," Polymer, vol. 38, No. 24, pp. 5931-5936, 1997.

Hickey, Alla, et al, "Mesh size and diffusive characteristics of semicrystalline poly(vinyl alcohol) membranes prepared by freezing/thawing techniques", Journal of Membrane Science, vol. 107, pp. 229-237, 1995.

Jagur-Grodzinski, Joseph, "Biomedical application of functional polymers" Reactive & Functional Polymers, vol. 39 pp. 99-138, 1999.

Kawanishi, Kazuo, et al. "Thermodynamic consideration of the sol-gel transition in polymer solutions", 35th Annual Mtg of the Society of Polymer Science, Japan 1986.

Kobayashi, Masanori, et al, "Development of an Artificial Meniscus using Polyvinyl alcohol-hydrogel for early return to, and continuance of, athletic life in sportspersons with severe meniscus injury. II: Animal experiments", The Knee, vol. 10, p. 53 (abstract), 2003.

Kobayashi, Masanori, et al, "Preliminary Study of polyvinyl alcohol-hydrogel (PVA-H) artifical meniscus", Biomaterials, vol. 24, pp. 639-647, 2003.

LeGeros, R., "Calcium Phosphates in Oral Biology and Medicine" Monograph in Oral Science, Karger, 1991, vol. 15, pp. 1-201.

Lester, Christopher, et al, "Physical Properties of Hydrogels Synthesized from Lyotropic Liquid Crystalline Templates", Chemical Materials, vol. 15, pp. 3376-3387, 2003.

Li, Bin, et al, "Synthesis of a Self-Gelatinizable Grafting Copolymer of Poly(vinyl Alcohol) for construction of an Amperometric Peroxidase Electrode," Analytical Biochemistry, vol. 256, pp. 130-132, 1998.

Lin-Gibson, Sheng, et al, "Synthesis and Characterization of PEG Dimethacrylates and Their Hydrogels "Biomacromolecules, vol. 5, pp. 1280-1287, 2004.

Lozinsky, Vladimir, et al, "Study of Cryostructuration of Polymer Systems. XIV. Poly(vinyl alcohol) Cryogels: Apparent Yield of the Freeze-Thaw-Induced Gelation of Concentrated Aqueous Solutions of the Polymer". Journal of Applied Polymer Sc., p. 1822-1831 2000.

Lozinsky, Vladimer,. et al. "Study of Cryostructuration of Polymer Systems. XVII. Poly(vinyl alcohol) Cryogels:Dynamics of the Cryotropic Gel Formation," Journal of Applied Polymer Science, vol. 77, pp. 2017-2023, 2000.

Lozinsky, Vladimer, et al., "On the Possibility of Mechanodestruction of Poly(vinyl alcohol) molecules under Moderate Freezing of its Concentrated Water Solution" Polymer Bulletin, vol. 15, pp. 333-340, 1986.

Lozinsky, Vladimer, et al, "Swelling behavior of poly9vinyl alcohol) cryogels employed as matrices for cell immobilization", Enzyme Microb. Technology, vol. 18, pp. 561-569. 1996.

Lu. Sanxiu, et al., "Photopolymerization of multilaminated poly(HEMA) hydrogels for controlled release," Journal of Controlled Release, vol. 57, pp. 291-300, 1999.

Mano, Valdir, et al., "Blends Composed of Poly(n-isopropylacrylamide) and an Ethylene/Vinyl Alcohol copolymer: Thermal and Morphological Studies", Journal of. Applied Polymer Science, vol. 91, pp. 501-505, 2004.

Mondino, A.V., et al, "Physical properties of gamma irradiated poly(vinyl alcohol) hydrogel preparations", Radiation Physics and Chemistry, vol. 55, pp. 723-726, 1999.

Moro, Toru, et al, "Surface Grafting of artifical joints with a biocompatible polymer for preventing periprosthetic osteolysis", Nature Materials, vol. 3, pp. 829-836, 2004.

Noguchi, Takashi, et al, "Poly(vinyl Alcohol) Hydrogel as an Artificial articular cartilage: Evaluation of Biocompatibility," Journal of Applied Biomaterials, vol. 2, pp. 101-107, 1991.

Oka, M., et al, "Development of artificial articular cartilage", Proc Insti. Mech. Engrs, vol. 214, Part H, pp. 59-68, 2000.

Park, Jae Hyung, et al, "Hydrogels based on poly(ethylene oxide) and poly(tetramethylene oxide) or poly(dimethyl siloxane). III. In Vivo biocompatibility and biostability," Journal Biomed. Materials Research, vol. 64A, pp. 309-319, 2003.

Park, Kyoung Ran, et al, "Synthesis of PVA/PVP hydrogels having two-layer by radiation and their physical properties," Radiation Physics and Chemistry, vol. 67, pp. 361-365, 2003.

Peppas, Nikolaos, et al., "Reinforced uncrosslinked poly(vinyl-alcohol) gels produced by cyclic freezing-thawing processes: a short review", Journal of Controlled Release, vol. 16 pp. 305-310, 1991.

Peppas, N.A., et al, "Physicochemical Foundations and Structural Design of Hydrogels in Medicine and Biology", Annuls Rev Biomedical Engrs., 02:9-20 2000.

Rao, Linfeng, et al, "Complexation of Eu(III) with alkyl-substituted malonamides in acctonitrile," Journal of Chemical Society, pp. 1939-1944, 2001.

Rosiak, J.M., et al., "Synthesis of Hydrogels by irradiation of polymers in aqueous solution" Radiation Physics and Chemistry, vol. 55, pp. 139-151, 1999.

Schmedlen, Rachael, et al, "Photocrosslinkable polyvinyl alcohol hydrogels that can be modified with cell adhesion peptides for use in tissue engineering", Biomaterials, vol. 23, pp. 4325-4332, 2002.

Stammen, J.A., et al, "Mechanical properties of a novel PVA hydrogel in shear and unconfined compression", Biomaterials, pp. 799-806 abstract only, 2001.

Suggs, Laura, et al, "In vitro cytotoxicity and in vivo biocompatibilith of Poly(propylene fumarate-co-ethylene glycol) hydrogels", Biomed. Materials Research, vol. 46, pp. 22-32, 1999.

Taguchi, Tetsushi, et al, "Hydroxyapatite Formation on/in Poly(vinyl alcohol) Hydrogel Matrices Using a Novel Alternate Soaking Process," Chemistry Letters, pp. 711-712, 1998.

Thomas, Jonathan, "Novel Associated PVA/PVP Hydrogels for Nucleus Pulposus Replacement", Thesis submitted at Drexel University, Sep. 2001.

Tripathy, T., et al., "Novel Flocculating agent based on sodium alginate and acrylamide", European Polymer Journal, vol. 35, pp. 2057-2072, 1999.

Ulanski, Piotr, et al., "OH-radical-induced crosslinking and strand breakage of poly(vinyl alcohol) in aqueous solution in the absence and presence of oxygen. A pulse radiolysis and product study", Macromol. Chem. Phys., vol. 195, pp. 1443-1461, 1994.

Urushizaki, Fumio, et al, "Swelling & Mechanical properties of poly(vinyl alcohol) hydrogels" International Journal of Pharmaceutics, vol. 58, pp. 135-142, 1990.

Ushio, Kazuyasu, et al, "Attachment of Artificial Cartilage to Underlying Bone", Journal Biomed. Mateiral Research, vol. 68B, pp. 59-68, 2004.

Ushio, K., et al, "Partial Hemiarthroplasty for the treatment of osteoncrosis of the femoral head", Journal of Bone Joint Surgery., vol. 85B, pp. 922-930, 2003.

Wang, Benlian, et al, "The influence of polymer concentration on the radiation-chemical yield of intermolecular crosslinking of poly(vinyl alcohol) by y-rays in deoxygenated aqueous solution", Radiation Physics and Chemistry, vol. 59 pp. 91-95, 2000.

West, Jennifer, et al, "Photopolymerized hydrogel materials for drug delivery applications," Reactive Polymers, vol. 25, pp. 139-147, 1995.

Yamaura, Kazuo, et al, "Properties of Gels Obtained by Freezing/Thawing of Poly(vinyl Alcohol)/Water/Dimethyl Sulfoxide Solutions," Journal of Applied Polymer Science, vol. 37 pp. 2709-2718, 1989.

Yokoyama, F., et al, "Morphology & Structure of highly elastic poly (vinyl alcohol) hydrogel prepared by repeated freezing-and-melting," Colloid & Polymer Science, vol. 264, pp. 595-601, 1986.

Zhang, Xianzheng, et al., "Synthesis & Characterizaton of partially biodegradable, temperature and pH sensitive Dex-MA/PNIPAAm hydrogels," Biomaterials, vol. 25, pp. 4719-4730, 2004.

Preliminary Report on Patentability and Written Opinion for PCT/US2008/071539 dated Mar. 2, 2010.

Preliminary Report on Patentability for PCT/US2008/071435 dated Feb. 9, 2010.

International Search Report and Written Opinion for PCT/US2006/006356 dated Jun. 22, 2006, 9 pgs.

EP Search Report for EP Application No. 06255568.5 dated Jun. 5, 2007.

EP Search Report for EP Application No. 06256525.4 dated May 10, 2007.

EP Search Report for EP Application No. 06256452.1 dated May 23, 2007.

International Search Report and Written Opinion for PCT/US2006/046725 dated Jul. 28, 2008, 20 pgs.

Preliminary Examination Report and Search Report for PCT/EP2005/010931 dated Feb. 6, 2007.

International Search Report and Written Opinion for PCT/US2007/064782 dated May 30, 2008.

International Search Report for PCT/US2008/071435 dated Feb. 12, 2009.

EPO Invitation to Pay additional fees and Annex to Search Report for PCT/US2006/046725 dated Apr. 22, 2008, 8 pages.

International Search Report and Written Opinion for PCT/US2008/071435 dated Feb. 5, 2009.

Preliminary Report on Patentability & Written Opinion for PCT/US2008/086817 dated Jul. 6, 2010.

International Search Report and Written Opinion for PCT/US2008/083213 dated May 8, 2009.

Preliminary Report on Patentability & Written Opinion for PCT/US2006/006356 dated Aug. 28, 2007.

EP Search Report for EP Application No. 050010009.9 dated Mar. 1, 2005.

* cited by examiner

ମULTI-POLYMER HYDROGELS

TECHNICAL FIELD

The present invention relates generally to a composition comprising multi-polymer hydrogel materials and methods of making the composition, and specifically to an implantable article formed from multi-polymer hydrogel materials.

BACKGROUND

Hydrogels are water-swellable or water-swollen materials having a structure defined by a crosslinked network of hydrophilic homopolymers or copolymers. The hydrophilic homopolymers or copolymers may or may not be water-soluble in free form, but in a hydrogel are rendered insoluble (but swellable) in water due to covalent, ionic, or physical crosslinking. In the case of physical crosslinking, the linking may take the form of entanglements, crystallites, or hydrogen-bonded structures. The crosslinks in a hydrogel provide structure and physical integrity to the network.

Hydrogels have been made from a variety of hydrophilic polymers and copolymers. Poly(ethylene glycol), poly(vinyl pyrrolidone), polyacrylamide, poly(hydroxyethyl methacrylate), and copolymers of the foregoing, are examples of polymers that may be used to make hydrogels. Hydrogels have also been made from biopolymers such as chitosan, agarose, hyaluronic acid and gelatin, in addition from semi-interpenetrating network ("IPN") hydrogels and gelatin crosslinked with poly(ethylene glycol) diacrylate.

Poly(vinyl alcohol) ("PVA") has been studied extensively for potential biomedical applications. PVA hydrogels can be produced, for example, from an aqueous solution via repeated freezing and thawing cycles that increase the order of the crystals, changing the dissolution properties, mesh size, and diffusion properties of the polymer.

Hydrogels have shown promise in biomedical and pharmaceutical applications, due, in part, to their high water content and rubbery or pliable nature, which may mimic natural tissue and may facilitate the release of bioactive substances at a desired physiological site. For example, hydrogels have been used or proposed for use in a variety of tissue treatment applications, including implants, tissue adhesives, bone grafts as well as in meniscus and articular cartilage replacement. Hydrogels may also act as a carrier for delivering bioactive substances including drugs, peptides, and proteins to a physiological site.

However, many biomedical applications require that the implanted article possess different characteristics, such as mechanical and chemical properties, at different locations or surfaces of the article. Thus, there is a need to provide hydrogel materials and articles that present different characteristics at different locations of the implanted article.

SUMMARY OF THE INVENTION

The present invention provides a multi-polymer hydrogel article comprising a first polymeric, water-swellable material and a second polymeric material. The multi-polymer hydrogel article has a first region that substantially comprises the first polymeric, water-swellable material, a second region adjacent the first region that comprises a mixture of the first polymeric, water-swellable material and the second polymeric material, and a third region adjacent the second region that substantially comprises the second polymeric material. The multi-polymer hydrogel article exhibits an increasing concentration gradient in the second polymeric material moving from the first region, through the second region, to the third region.

The present invention also provides a method of forming a multi-polymer hydrogel article. The inventive method comprises forming a hydrogel structure comprising a first polymeric, water-swellable material. An aerogel structure comprising a plurality of open pores is formed by dehydrating the hydrogel structure. The aerogel structure is then contacted with a second polymeric material. The second polymeric material incorporates into at least a portion of the plurality of open pores in the aerogel structure to form a multi-polymer hydrogel article. The resulting multi-polymer hydrogel article is then rehydrated.

DETAILED DESCRIPTION

The present invention provides for a multi-polymer hydrogel article comprising a first polymeric, water-swellable material and a second polymeric material. The multi-polymer hydrogel article is organized into a first, second, and third region, wherein the first region substantially comprises the first polymeric, water-swellable material, the second region adjacent the first region comprises a mixture of the first polymeric, water-swellable material and the second polymeric material, and the third region adjacent the second region substantially comprises the second polymeric material. Further, the second polymeric material exhibits an increasing concentration gradient moving from the first region, through the second region, to the third region. In one embodiment, the second polymeric material is a water-swellable material.

As used in this specification, the terms "water-swellable" or "hydrogel" indicate that the article is able to take on and retain water within a network of polymers.

Suitable water-swellable materials include at least one of a hydrophilic polymer, a homopolymer, a combination of a hydrophilic polymer and a hydrophobic polymer, a blend of polymers, a copolymer, or a thermoplastic material, or combinations thereof. In one embodiment, the water-swellable material is selected from the group consisting of polymers and copolymers of polyvinyl alcohol, polyglycols, polyethylene glycol dimethacrylate, polyethylene glycol diacrylate, polyhydroxyethyl methacrylate, polyvinyl pyrrolidone, polyacrylamide, polyacrylic acid, hydrolyzed polyacrylonitrile, polyethyleneimine, ethoxylated polyethyleneimine, polyallyl alcohol, and polyallylamine, and combinations thereof.

In some embodiments, the second polymeric material is a polyurethane elastomer, silicone elastomer, hydrogel, or lyogel, or combinations thereof. In one embodiment, the first polymeric, water-swellable material and the second polymeric material comprise a common monomer. The second polymeric material may also be water-swellable, with the first and second water-swellable materials being different, with a common monomer or without a common monomer. For example, in one embodiment, the first polymeric, water-swellable material is a polyvinyl alcohol (PVA)/polyethylene-co-vinyl alcohol (EVAL) copolymer and the second polymeric material is polyvinyl alcohol (PVA). In some embodiments, the first polymeric, water-swellable material, the second polymeric material, the aerogel structure, and/or the multi-polymer hydrogel article is thermoplastic. Further examples of suitable materials to be used as the first polymeric, water-swellable material and/or the second polymeric material can be found in U.S. patent application Ser. No. 11/614,389, incorporated by reference herein in its entirety.

The organization of the multi-polymer hydrogel article is such that the first region extends from a first point to a first interface with the second region, the second region extends from the first interface to a second interface with the third region, and the third region extends from the second interface to a second point. Further, the percent volume ratio of the first polymeric, water-swellable material to the second polymeric material is about 100:0 at the first point and about 0:100 at the second point and continuously changes from 100:0 at the first point to 0:100 at the second point. Each of the first and second points may reside at exterior surfaces of the article, or may reside interiorly within the respective first and third regions.

The present invention also provides a method of forming a multi-polymer hydrogel article. The method comprises (a) forming a hydrogel structure comprising a first polymeric, water-swellable material, (b) creating an aerogel structure comprising a plurality of open pores by dehydrating the hydrogel structure, (c) contacting the aerogel structure with a second polymeric material to incorporate the second polymeric material into at least a portion of the plurality of open pores to form a multi-polymer hydrogel article, and (d) rehydrating the multi-polymer hydrogel article.

The method of the present invention may be used to impart desireable characteristics in a hydrogel material or device, such as reinforcing particular areas, providing hoop stress support, creating transition zones between different materials, and/or changing mechanical properties, e.g., compressive modulus, tensile strength, etc.

In one embodiment, forming the hydrogel structure comprises casting, injection molding, or compression molding the first polymeric, water-swellable material into a shape. In another embodiment, forming the hydrogel structure further comprises dip coating, casting or molding the first polymeric, water-swellable material at least partially encompassing a third sacrificial material. In some embodiments, the third sacrificial material is soluble in an aqueous solution. The third sacrificial material may comprise a variety of materials including sugars, waxes, gelatins, salts, low molecular weight water-soluble polymers, ice, and biodegradable polymers, and combinations thereof.

In one embodiment of the present method, the third sacrificial material is dissolved to form a void at least partially encompassed by the first polymeric, water-swellable material. In various embodiments, the third sacrificial material is dissolved in vivo. In one embodiment, the void is limited at its periphery by the first polymeric, water-swellable material such that the first polymeric, water-swellable material substantially surrounds the void. In some embodiments, the first polymeric, water-swellable material forms a ballon or a bubble. The void and/or the hydrogel structure may be tailored to any desired shape and size. In some embodiments, the void created by the third sacrificial material may be at least partially filled with a second polymeric material that is in liquid form. The liquid polymer may be injected by a needle or cannula into the void formed by the third sacrificial material.

In another embodiment, the third sacrifical material is included in the first polymeric, water-swellable material such that when the third sacrifical material is dissolved, open pores are formed in addition to those formed when creating the aerogel structure. In some embodiments, the third sacrificial material is soluble in an aqueous solution. The third sacrificial material may comprise a variety of materials including sugars, waxes, gelatins, salts, low molecular weight water-soluble polymers, ice, and biodegradable polymers, and combinations thereof.

In one embodiment, the formation of the hydrogel structure includes using a surfactant or rapid agitation to create spheres, rods, globules, ellipsoidal shapes, cylindrical shapes, and/or disc-like shapes. In one embodiment, a surfactant is used in the polymerization process to create hydrogel beads, for example, polymerization of hydroxymethylmethacrylate in a surfactant. In another embodiment, the surfactant may be polymerized in a self-emulsifying polymerization to create the hydrogel beads, for example, the polymerization of sodium methacrlate in water. Monomers that may be polymerized in the prescense of surfactants to create hydrogel beads may include glycidyl methacrylate modified hyaluronate, acrylate modified polyethylene glycol, or the polymerization of vinyl acetate followed by post hydrolysis to create polyvinyl alcohol. Suitable surfactants for these polymerizations may include perfluorocarboxlyic acid salts, tetraethylene glycol dodecyl ether, decaethylene glycol hexadecyl ether, carboxylic acid salts, Alkanol®, Merpol®, Brij®, Adogen®, Igepal®, Tergitol®, or Triton®.

The aerogel structure is created by dehydrating, e.g. removing water and/or plasticizers, from the hydrogel structure. It may be understood that dehydration includes partial to complete removal of water and/or plasticizers from the hydrogel structure. In various embodiments, the water and/or plasticizer is removed from the hydrogel structure by, for example, heating, evaporating, subjecting to a vacuum, freeze-drying, or solvent exchange, or combinations thereof. In embodiments where the water and/or plasticizer is partially removed from the hydrogel structure, a semiporous material is created. In some embodiments, after dehydrating the hydrogel structure to create the aerogel structure, the aerogel structure is formed into a desired shape. Forming the aerogel structure includes cutting, molding, and/or shaping the aerogel structure. In some embodiments, water-swellable sheets may be dehydrated before creating a desired shape.

After formation of the aerogel structure, the aerogel structure is contacted with a second polymeric material. As used herein "contacted" includes filling, pressing, interlocking, impregnating, penetrating or intercalating. Furthermore, the aerogel structure may be contacted by the second polymeric material in a variety of ways including immersing at least a portion of the aerogel structure in the second polymeric material, injecting the second polymeric material into at least a portion of the aerogel structure, compressing the second polymeric material into at least a portion of the aerogel structure, and contacting less than the entire surface area of the aerogel structure with the second polymeric material.

In an alternative embodiment, the first polymeric, water-swellable material, absent formation of the aerogel structure, may be contacted with the second polymeric material and introduced into the first polymeric, water-swellable material by solvent bonding techniques. Solvent bonding requires compatible solvents for the first polymeric, water-swellable material and the second polymeric material. The solvent bonding creates an interlocking of the two polymer layers. Compatible solvents may include tetrahydrofuran, toluene, dimethylformamide, dimethylacetamide, acetone, acetonitrile, cyclohexane, cyclopentane, 1,4-dioxane, ethyl acetate, glyme, methyl tert-butyl ether, methyl ethyl ketone, pyridine, water, dimethylsulfoxide, or chlorobenzene, or combination thereof. The subsequent solvent bonded structure formed following contact between the first polymeric, water-swellable material and the second polymeric material is amenable to all the embodiments described herein.

The method of the present invention results in the formation of a multi-polymer hydrogel article comprising the first polymeric, water-swellable material and the second polymeric material. The multi-polymer hydrogel article is organized into a first region substantially comprising the first polymeric, water-swellable material, a second region adjacent the first region comprising a mixture of the first polymeric, water-swellable material and the second polymeric material, and a third region adjacent the second region substantially comprising the second polymeric material. Further, the second polymeric material exhibits an increasing concentration gradient moving from the first region, through the second region, to the third region.

Additionally, the first region extends from a first point to a first interface with the second region, the second region extends from the first interface to a second interface with the third region and includes therein a second point, and the third region extends from the second interface to a third point. In one embodiment, the multi-polymer hydrogel article formed by the present method has a percent volume ratio of the first polymeric, water-swellable material to the second polymeric material that continuously changes from about 100:0 at the first point, to about 50:50 at the second point, to about 0:100 at the third point. In one embodiment, pore blockers are present during the present method such that some portion of the pores in the aerogel structure are resistant to penetration by the second polymeric material. In embodiments where a pore blocker is present, the second point is moved towards the third point in the multi-polymer hydrogel article. Pore blockers that may be used in the present method include sugars, salts, low molecular weight water-soluble polymers, waxes, liquids, and biodegradable polymers, and combinations thereof.

In addition to the incorporation of the second polymeric material into at least a portion of the plurality of open pores in the aerogel structure to form a multi-polymer hydrogel article, in some embodiments, the second polymeric material is also introduced into the void created by dissolving the third sacrificial material such as sugars, salts, or waxes. In another embodiment, a material is introduced into the void created by dissolving the third sacrificial material and may include materials such as lyogels, hydrogels, monomers, beads, urethanes, acrylates, methacrylates, or other injectable polymeric materials or precursors. In various embodiments, the second polymeric material may contact the first polymeric, water-swellable material in situ and/or be cured in situ as part of an implantation procedure or cured ex-vivo before implantation.

In one embodiment, the aerogel structure is contacted with the second polymeric material under pressure. Using the previously described organization of the resultant multi-polymer hydrogel article where the first region extends from a first point to a first interface with the second region, the second region extends from the first interface to a second interface with the third region and includes therein a second point, and the third region extends from the second interface to a third point and where a percent volume ratio of the first polymeric, water-swellable material to the second polymeric material continuously changes from about 100:0 at the first point, to about 50:50 at the second point, to about 0:100 at the third point, the affect of contacting the aerogel structure with the second polymeric material under pressure is to move the second point towards the first point. The extent of the movement of the second point towards the first point is affected by many factors including the amount of pressure exerted on the second polymeric material.

In yet another embodiment of the present method, a multilayered, multi-polymer hydrogel article is produced. In one embodiment, at least one of the method steps (a-d) described above is repeated. For instance, following contacting of the aerogel with the second polymeric material, the resulting aerogel structure incorporating the second polymeric material is dehydrated to form a second aerogel structure. This second aerogel structure can be contacted with a third polymeric material such that the third polymeric material incorporates into at least a portion of the second aerogel structure. The process can be repeated such that n aerogel structures are contacted with n+1 polymeric materials and with each cycle of dehydration and incorporation, another layer is added to the resultant multi-polymer hydrogel article. The n+1 polymeric material can be any of the potential materials described for either the first polymeric, water-swellable material or the second polymeric material. Also, any of the n aerogel structures are subject to the embodiments described above for the aerogel structure. In various embodiments, the multilayers are comprised of different polymeric materials or the same polymeric material. In one embodiment, the multilayered, multi-polymer hydrogel article is composed of variations of the same polymer. For instance, the polymer may vary by concentration, molecular weight, degree of branching, tacticity, extent of crosslinking, etc.

In still another embodiment, the multilayered, multi-polymer hydrogel article can be accomplished utilizing insert-molding techniques known to one skilled in the art. Examples of methods to create the layering may include liquid injection molding. Compression molding may also be used and insures good interlocking of the first polymeric, water-swellable material and the second polymeric material.

In another embodiment, a multilayered, multi-polymer hydrogel article may be formed using solvent bonding by at least partially covering a first polymeric, water-swellable material with a second polymeric material, both containing compatible solvents, to create a multi-polymer hydrogel article. The multi-polymer hydrogel article may then be contacted with a third polymeric material, also containing compatible solvents, resulting in a multilayered, multi-polymer hydrogel article. The process may be repeated such that each cycle of incorporation results in another layer being added to the resultant multi-polymer hydrogel article. In various embodiments, the multilayers are comprised of different polymeric materials or the same polymeric material. In one embodiment, the multilayered, multi-polymer hydrogel article is composed of variations of the same polymer. For instance, the polymer may vary by concentration, molecular weight, extent of crosslinking, etc.

The present method for forming a multi-polymer hydrogel article may also include crosslinking of all or a portion of the multi-polymer hydrogel article. In various embodiments, crosslinking can occur by radiation crosslinking, physical crosslinking, or chemical crosslinking, or combinations thereof. Examples of radiation crosslinking includes exposing the multi-polymer hydrogel article to at least one of visible light radiation, infrared radiation, ultraviolet radiation, electron beam radiation, gamma radiation, or x-ray radiation. An example of physical crosslinking is exposing the multi-polymer hydrogel article to freezing and thawing. Examples of chemical crosslinking includes exposing the multi-polymer hydrogel article to a monoaldehyde or a diisocyanate. Crosslinking may be carried out after forming the hydrogel structure, after forming the multi-polymer hydrogel article, after shaping the multi-polymer hydrogel article into a desired shape, after in situ formation of the article, or at any other suitable point during processing.

The multi-polymer hydrogel article of the present invention may be suitable for use in a wide variety of applications, including tissue replacement or augmentation, biomedical applications, and pharmaceutical applications. Also, the article will have utility for many orthopedic conditions, particularly those that involve repair of a cartilage, repair of soft tissue defects, e. g., treating damaged or diseased hyaline cartilage, replacement of damaged cartilage surface, and use in spinal discs. The article of the present invention can be used as an implant to replace at least a portion of an artificial hip, hip liner, knee, knee liner, disk replacement, shoulder, elbow, foot, ankle, finger, or mandible.

The following examples are provided to illustrate the invention and are not intended to limit the same.

EXAMPLE 1

Synthesis of the First Polymeric, Water-Swellable Material

To a 1000 ml beaker equipped with a mechanical stirrer was added 60 g polyvinyl alcohol, 30 ml deionized water, and 270 ml of dimethylsulfoxide (DMSO). The polyvinyl alcohol was 99+ % hydrolyzed with an average molecular weight of 124 kiloDalton (kDa) to 186 kDa and was used as received from Sigma-Aldrich (St. Louis, Mo.). The DMSO was used as received from Sigma-Aldrich and contained $\leqq 0.4\%$ water. The solution was heated to 90° C. for three hours.

After three hours, the solution was poured into one-$cm^3$ aluminum molds. The solution was allowed to cool slowly to room temperature, and the aluminum molds were then placed into a freezer at −30° C. for three hours. The aluminum molds were removed from the freezer.

The resulting material was translucent, flexible, and pliable. The one $cm^3$ polymeric samples were extracted with 700 ml reagent-grade alcohol (ethanol) followed by solvent exchange with deionized water over a three-day period. The resulting material remained translucent, flexible, and pliable.

Dehydration was performed on a vacuum glass Schlenck line by using a freeze-thaw technique in which the sample was frozen followed by evacuation of the liquid vapor phase. The freeze-thaw procedure was performed as follows: the samples were frozen at −196° C. and a dynamic vacuum was placed on the sample as it warmed to room temperature. The freeze-dried samples served as the aerogel structure.

Synthesis of the Second Polymeric Material

To a one-gallon sigma mixer/extruder (Jaygo Incorporated, New Jersey) fitted with a 3 mm fiber die was added 625.89 g polyethylene-co-vinyl alcohol, 100 ml of water, 1350 g DMSO, and 626.79 g polyvinyl alcohol. The materials were mixed at 240° F. (116° C.) for 70 minutes. The polyvinyl alcohol was 99+ % hydrolyzed with an average molecular weight of 146,000 to 186,000 and was used as received from Sigma-Aldrich. The polyethylene-co-vinyl alcohol had an ethylene content of 44 mole-percent and was used as received from Sigma-Aldrich. The DMSO was used as received from Sigma-Aldrich and contained $\leqq 0.4\%$ water.

After 70 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Synthesis of the Multi-Polymer Hydrogel Article

The multi-polymer hydrogel article was formed on a Morgan Press ram injection molder G-100T from Morgan Industries Inc. (Long Beach, Calif.). The aerogel structure was placed in an aluminum mold. The second polymeric material pellets were placed into the barrel of the injection molder. The material was injection molded at 270° C. barrel and 280° C. nozzle temperature. Injection pressure was 7000 psi with 18 tons clamping pressure. After injection, the mold was cooled with circulating water at 10° C. for five minutes prior to removing the sample. The multi-polymer hydrogel article was extracted with 700 ml reagent-grade alcohol (ethanol) followed by solvent exchange with deionized water over a three-day period. The resulting multi-polymer hydrogel article showed a transparent material in the middle of the sample (substantially comprising the first polymeric material) transitioning to an opaque material in the periphery (substantially comprising the second polymeric material). The material in the article remained flexible and pliable.

EXAMPLE 2

Synthesis of the First Polymeric, Water-Swellable Material

To a 1000 ml beaker equipped with a mechanical stirrer was added 60 g polyvinyl alcohol, 30 ml deionized water, and 270 ml of DMSO. The polyvinyl alcohol was 99+ % hydrolyzed with an average molecular weight of 124 kDa to 186 kDa and was used as received from Sigma-Aldrich. The DMSO was used as received from Sigma-Aldrich and contained $\leqq 0.4\%$ water. The solution was heated to 90° C. for three hours.

After three hours, the solution was cast between two glass plates to create a hydrogel structure as a sheet. The solution was allowed to cool slowly to room temperature, and the plates were then placed into a freezer at −30° C. for three hours. The plates were removed from the freezer.

The resulting material was translucent, flexible, and pliable. The polymeric sample was extracted with 700 ml reagent-grade alcohol (ethanol) followed by solvent exchange with deionized water over a three-day period. The resulting material remained translucent, flexible, and pliable.

Dehydration was performed on a vacuum glass Schlenck line by using a freeze-thaw technique. The samples were frozen at −196° C. and a dynamic vacuum was placed on the sample as it warmed to room temperature. The freeze-dried samples served as the aerogel structure.

Synthesis of the Second Polymeric Material

To a Jaygo one-gallon sigma mixer/extruder fitted with a 3 mm fiber die was added 625.89 g polyethylene-co-vinyl alcohol, 100 ml of water, 1350 g DMSO, and 626.79 g polyvinyl alcohol. The materials were mixed at 240° F. (116° C.) for 70 minutes. The polyvinyl alcohol was 99+ % hydrolyzed with an average molecular weight of 146,000 to 186,000 and was used as received from Sigma-Aldrich. The polyethylene-co-vinyl alcohol had an ethylene content of 44 mole-percent and was used as received from Sigma-Aldrich. The DMSO was used as received from Sigma-Aldrich and contained $\leqq 0.4\%$ water.

After 70 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Synthesis of the Multi-Polymer Hydrogel Article

The multi-polymer hydrogel article was formed on a Morgan-Press G-100T ram injection molder. The aerogel structure was placed in an aluminum mold. The second polymeric material pellets were placed into the barrel of the injection molder. The material was injection molded at 270° C. barrel and 280° C. nozzle temperature. Injection pressure was 7000 psi with 18 tons clamping pressure. After injection, the mold was cooled with circulating water at 10° C. for five minutes prior to removing the sample. The multi-polymer hydrogel article was extracted with 700 ml reagent-grade alcohol (ethanol) followed by solvent exchange with deionized water over a three-day period. The resulting multi-polymer hydrogel article showed a transparent material in the middle of the sample (substantially comprising the first polymeric material) transitioning to an opaque material in the periphery (substantially comprising the second polymeric material). The multi-polymer hydrogel article remained flexible and pliable.

EXAMPLE 3

Synthesis of the First Polymeric, Water-Swellable Material

To a 1000 ml beaker equipped with a mechanical stirrer was added 20 g polyvinyl alcohol, 10 ml deionized water, and 170 ml of DMSO. The polyvinyl alcohol was 99+% hydrolyzed with an average molecular weight of 124 kDa to 186 kDa and was used as received from Sigma-Aldrich. The DMSO was used as received from Sigma-Aldrich and contained $\leq 0.4\%$ water. The solution was heated to 80° C. for three hours.

After three hours, the solution was poured into a 50 ml flask to form a ¼ inch layer. The layer was allowed to cool to room temperature. A molded piece of sugar was placed on top of the layer and additional polymer solution was poured on top of the layer to form the hydrogel structure. The hydrogel structure was quickly frozen to −30° C. in a methanol/liquid nitrogen slush bath. The hydrogel structure was allowed to warm to room temperature over a two hour period. The hydrogel structure was submersed in methanol for 12 hours followed by solvent exchange in water for three days to dissolve the sugar. The hydrogel structure was then dehydrated and vacuum dried to produce a void.

Synthesis of the Second Polymeric Material

To a 50 ml beaker equipped with a mechanical stirrer was added 15 ml DMSO, 1 ml deionized water, 1.5 g polyvinyl alcohol and 1 g polyethylene-co-vinyl alcohol. The materials were mixed at 80° C. for 3 hours.

Synthesis of the Multi-Polymer Hydrogel Article

The second polymeric material was injected into the void created by the sugar using an 18-gauge needle and syringe. The final article was placed in water for solvent exchange. The subsequent article was cross-sectioned showing that the void was in fact filled with the second polymeric material and the material was attached to the first polymeric material.

Characterization

Mechanical performance properties for selected hydrogels were measured on a Model 3345 from Instron Corporation. The sample from Example 1 showed a push out strength of 1649 psi, which indicates that the first polymeric, water-swellable material and the second polymeric material are interlocked. Push out strength refers to the amount of force required to separate the first polmeric material from the second polymeric material. In this case, the two materials have different mechanical strengths. The high push out strength shows that the two materials were in fact bound together.

What is claimed is:

1. A multi-polymer hydrogel article comprising a first polymeric, water-swellable material and a second polymeric material, wherein a first region of the article substantially comprises the first polymeric, water-swellable material, a second region adjacent the first region comprises a mixture of the first polymeric, water-swellable material and the second polymeric material, and a third region adjacent the second region substantially comprises the second polymeric material, and wherein the second polymeric material exhibits an increasing concentration gradient moving from the first region, through the second region, to the third region.

2. The multi-polymer hydrogel article of claim 1, wherein the second polymeric material is a water-swellable material.

3. The multi-polymer hydrogel article of claim 2, wherein the water-swellable second polymeric material is at least one of a hydrophilic polymer, a homopolymer, a combination of a hydrophilic polymer and a hydrophobic polymer, a blend of polymers, a copolymer, or a thermoplastic material, or combinations thereof.

4. The multi-polymer hydrogel article of claim 2, wherein the water-swellable second polymeric material is selected from the group consisting of polymers of polyvinyl alcohol, polyglycols, polyethylene glycol dimethacrylate, polyethylene glycol diacrylate, polyhydroxyethyl methacrylate, polyvinyl pyrrolidone, polyacrylamide, polyacrylic acid, hydrolyzed polyacrylonitrile, polyethyleneimine, ethoxylated polyethyleneimine, polyallyl alcohol, and polyallylamine, and combinations thereof.

5. The multi-polymer hydrogel article of claim 1, wherein the first polymeric, water-swellable material is at least one of a hydrophilic polymer, a homopolymer, a combination of a hydrophilic polymer and a hydrophobic polymer, a blend of polymers, a copolymer, or a thermoplastic material, or combinations thereof.

6. The multi-polymer hydrogel article of claim 1, wherein the first polymeric, water-swellable material is selected from the group consisting of polymers of polyvinyl alcohol, polyglycols, polyethylene glycol dimethacrylate, polyethylene glycol diacrylate, polyhydroxyethyl methacrylate, polyvinyl pyrrolidone, polyacrylamide, polyacrylic acid, hydrolyzed polyacrylonitrile, polyethyleneimine, ethoxylated polyethyleneimine, polyallyl alcohol, and polyallylamine, and combinations thereof.

7. The multi-polymer hydrogel article of claim 1, wherein the second polymeric material is a polyurethane elastomer, silicone elastomer, hydrogel, or lyogel, or combinations thereof.

8. The multi-polymer hydrogel article of claim 1, wherein the first polymeric, water-swellable material is a polyvinyl alcohol (PVA)/polyethylene-co-vinyl alcohol (EVAL) copolymer and the second polymeric material is polyvinyl alcohol (PVA).

9. The multi-polymer hydrogel article of claim 1, wherein the first polymeric, water-swellable material and the second polymeric material comprise a common monomer.

10. The multi-polymer hydrogel article of claim 1, wherein the first region extends from a first point to a first interface with the second region, the second region extends from the first interface to a second interface with the third region, and the third region extends from the second interface to a second point;

wherein a percent volume ratio of the first polymeric, water-swellable material to the second polymeric material is about 100:0 at the first point and about 0:100 at the second point.

11. The multi-polymer hydrogel article of claim 10, wherein the percent volume ratio continuously changes from 100:0 at the first point to 0:100 at the second point.

12. An implantable article produced by a process comprising: (a) forming a hydrogel structure comprising a first polymeric, water-swellable material, (b) creating an aerogel structure comprising a plurality of open pores by dehydrating the hydrogel structure, (c) contacting the aerogel structure with a second polymeric material to incorporate the second polymeric material into at least a portion of the plurality of open pores to form the multi-polymer hydrogel article, and (d) rehydrating the multi-polymer hydrogel article and wherein the multi-polymer hydrogel article is organized into a first region substantially comprising the first polymeric, water-swellable material, a second region adjacent the first region comprising a mixture of the first polymeric, water-swellable material and the second polymeric material, and a third region adjacent the second region substantially comprising the second polymeric material such that the second polymeric material exhibits an increasing concentration gradient moving from the first region, through the second region, to the third region.

13. The implantable article of claim 12 wherein the implantable article comprises at least portions of an artificial hip, hip liner, knee, knee liner, disk replacement, shoulder, elbow, foot, ankle, finger, or mandible.

* * * * *